United States Patent
Canady et al.

(10) Patent No.: US 10,973,564 B2
(45) Date of Patent: Apr. 13, 2021

(54) INTEGRATED COLD PLASMA AND HIGH FREQUENCY PLASMA ELECTROSURGICAL SYSTEM AND METHOD

(71) Applicant: U.S. Patent Innovations LLC, Takoma Park, MD (US)

(72) Inventors: Jerome Canady, Lakeland, FL (US); Alexey Shashurin, Rockville, MD (US); Michael Keidar, Baltimore, MD (US); Taisen Zhuang, Rockville, MD (US)

(73) Assignee: U.S. Patent Innovations LLC, Takoma Park, MD (US)

( * ) Notice: Subject to any disclaimer, the term of this patent is extended or adjusted under 35 U.S.C. 154(b) by 357 days.

(21) Appl. No.: 15/991,609

(22) Filed: May 29, 2018

(65) Prior Publication Data

US 2018/0271582 A1    Sep. 27, 2018

Related U.S. Application Data (63) Continuation-in-part of application No. 14/725,167, filed on May 29, 2015, now Pat. No. 9,999,462.
(Continued)

(51) Int. Cl.
*A61B 18/12*     (2006.01)
*A61B 18/04*     (2006.01)
(Continued)

(52) U.S. Cl.
CPC ........ *A61B 18/1206* (2013.01); *A61B 18/042* (2013.01); *H05H 1/46* (2013.01);
(Continued)

(58) Field of Classification Search
CPC .............. A61B 18/042; A61B 18/1206; A61B 2018/00172; A61B 2018/00178;
(Continued)

(56) References Cited

U.S. PATENT DOCUMENTS 4,040,426 A    8/1977   Morrison
4,429,694 A    2/1984   McGreevy
(Continued)

FOREIGN PATENT DOCUMENTS

WO    2012061535    5/2012

OTHER PUBLICATIONS

A. Erwine, "ESU-2000 Series Product Overview A Paradigm Shift in Electrosurgery Testing Technology and Capability is Here," BC Group International, inc. (2007).
(Continued)

*Primary Examiner* — Daniel W Fowler
*Assistant Examiner* — Tigist S Demie
(74) *Attorney, Agent, or Firm* — 24IP Law Group USA, PLLC; Timothy Dewitt (57) ABSTRACT

An integrated gas-enhanced electrosurgical generator. The generator comprises a high frequency power module, a low frequency power module and a gas module. The high frequency power module adapted to generate an electrical energy having a band of frequencies centered around a first frequency, wherein the electrical energy has a first power as the first frequency and a second power lower than the first power at a second frequency lower than the first frequency. The low frequency power module having an input connected to an output of the high frequency module. The low frequency module comprises a resonant transformer comprising a ferrite core, a primary coil and a secondary coil, the secondary coil having a larger number of turns than the primary coil, wherein the resonant transformer has a resonant frequency equal to the second frequency. The gas module is adapted to control a flow of an inert gas.

5 Claims, 7 Drawing Sheets

Related U.S. Application Data (60) Provisional application No. 62/004,360, filed on May 29, 2014.

(51) Int. Cl.
*A61B 18/14* (2006.01)
*H05H 1/46* (2006.01)
*A61B 18/00* (2006.01)

(52) U.S. Cl.
CPC ..... *A61B 18/14* (2013.01); *A61B 2018/00172* (2013.01); *A61B 2018/00583* (2013.01); *A61B 2018/1286* (2013.01); *H05H 2001/4645* (2013.01); *H05H 2001/4682* (2013.01); *H05H 2245/122* (2013.01)

(58) Field of Classification Search
CPC .......... A61B 2018/00583; A61B 18/14; A61B 2018/1286; H05H 1/46; H05H 2001/4645; H05H 2001/4682; H05H 2245/122
See application file for complete search history.

(56) References Cited

U.S. PATENT DOCUMENTS

| | | | |
|---|---|---|---|
| 4,781,175 | A | 11/1988 | McGreevy |
| 5,088,997 | A * | 2/1992 | Delahuerga .......... A61B 18/042 606/42 |
| 5,098,430 | A | 3/1992 | Fleenor |
| 5,207,675 | A | 5/1993 | Canady |
| 5,217,457 | A | 6/1993 | Delahuerga |
| 6,149,648 | A | 11/2000 | Cosmescu |
| 7,517,347 | B2 | 4/2009 | Hug et al. |
| 2006/0052774 | A1 | 3/2006 | Garrison |
| 2006/0122595 | A1 | 6/2006 | Farin |
| 2007/0225699 | A1 | 9/2007 | Goble |
| 2010/0145253 | A1* | 6/2010 | Gutsol .................. A61B 18/042 604/20 |
| 2013/0237982 | A1* | 9/2013 | Rencher ................ A61B 18/10 606/39 |
| 2015/0282862 | A1* | 10/2015 | Warren .............. A61B 18/1206 606/34 |

OTHER PUBLICATIONS

"Force Argon II System," Valleylab 2006.
"Argon-Plasma Koagulation," GMS Krankenhaushygiene Interdisziplinar 2008, vol. 3(1), ISSN 1863-5245.
"Valleylab Force Argon II Argon Enhanced Electrosurgical System," 1997.
A. Fridman, Plasma Chemistry (Cambridge University Press, 2008).
G. Fridman, G. Friedman, A. Gutsol, A. B. Shekhter, V. N. Vasilets, and A. Fridman "Applied Plasma Medicine," Plasma Processes Polym. 5, 503 (2008).
E. Stoffels, Y. Sakiyama, and D.B. Graves "Cold Atmospheric Plasma: Charged Species and Their Interactions With Cells and Tissues," IEEE Trans. Plasma Sci. 36, 1441 (2008).
X. Lu, Y. Cao, P. Yang, Q. Xiong, Z. Xiong, Y. Xian, and Y. Pan "An RC Plasma Device for Sterilization of Root Canal of Teeth," IEEE Trans. Plasma Sci. 37, 668 (2009).
K.H. Becker, K.H. Shoenbach and J.G. Eden "Microplasma and applications," J. Phys. D.:Appl.Phys. 39, R55-R70 (2006).
E. Stoffels, I.E. Kieft, R.E.J Sladek, L.J.M van den Bedem, E.P. van der Laan, M. Steinbuch "Plasma needle for in vivo medical treatment: recent developments and perspectives," Plasma Sources Sci. Technol. 15, S169-S180 (2006).
M. Keidar, A. Shashurin, R. Ravi, R. Guerrero-Preston and B. Trink, British Journal of Cancer 105, 1295 (2011).
A. Shashurin, M.Keidar, S.Bronnikov, R.A. Jurjus, M.A. Stepp, Appl.Phys.Let. 92, 181501 (2008).
A. Shashurin, M.A. Stepp, T.S. Hawley, S. Pal-Ghosh, L. Brieda, S. Bronnikov, R.A. Jurjus, M. Keidar, "Influence of cold plasma atmospheric jet on integrin activity of living cells," Plasma Process. Polym. 7 294 (2010).
O. Volotskova, T. S. Hawley, M. A. Stepp & M. Keidar, "Targeting the cancer cell cycle by cold atmospheric plasma," Scientific Reports, 2:636, Sep. 6, 2012.
Maynard, J.E., "Tuned Transformers . . . Design of these electronic units simplified by means of universal performance curves," General Electric Review, Oct. 1943 pp. 559-609.
Huffman, B., "Parasitic Capacitance Effects in Step-up Transformer Design," Linear Technology, Application Note 39, Feb. 1990.
Transformer and Inductor Design Handbook, Chapter 17 (2004).

* cited by examiner

INTEGRATED COLD PLASMA AND HIGH FREQUENCY PLASMA ELECTROSURGICAL SYSTEM AND METHOD

CROSS-REFERENCE TO RELATED APPLICATIONS

The present application is a continuation-in-part of U.S. Non-provisional application Ser. No. 14/725,167, filed on May 29, 2015, entitled "Integrated Cold Plasma and High Frequency Plasma Electrosurgical System and Method," which claims the benefit of the filing date of U.S. Provisional Patent Application Ser. No. 62/004,360 filed on May 29, 2014.

The aforementioned provisional patent application is hereby incorporated by reference in its entirety.

STATEMENT REGARDING FEDERALLY SPONSORED RESEARCH OR DEVELOPMENT

None.

BACKGROUND OF THE INVENTION

Field of the Invention

The present invention relates to a systems for producing cold plasmas.

Background of the Related Art

The unique chemical and physical properties of cold atmospheric plasmas enable their numerous recent applications in biomedicine including sterilization, the preparation of polymer materials for medical procedures, wound healing, tissue or cellular removal and dental drills. A. Fridman, Plasma Chemistry (Cambridge University Press, 2008); G. Fridman, G. Friedman, A. Gutsol, A. B. Shekhter, V. N. Vasilets, and A. Fridman "Applied Plasma Medicine", *Plasma Processes Polym.* 5, 503 (2008); E. Stoffels, Y. Sakiyama, and D. B. Graves "Cold Atmospheric Plasma: Charged Species and Their Interactions With Cells and Tissues" *IEEE Trans. Plasma Sci.* 36, 1441 (2008); X. Lu, Y. Cao, P. Yang, Q. Xiong, Z. Xiong, Y. Xian, and Y. Pan "An RC Plasma Device for Sterilization of Root Canal of Teeth" *IEEE Trans. Plasma Sci.* 37, 668 (2009).

Plasma-based nitrogen oxide (NO) therapy demonstrated huge potential for stimulation of regenerative processes and wound healing. The work uncovering function of nitrogen oxide as a signal molecule was awarded by the Nobel Prize in medicine and biology in 1999. NO-therapy demonstrated tremendous effect of acceleration of healing of ulcer, burns and serious wounds. Other experimental evidence supports efficiency of cold plasmas produced by dielectric barrier discharge for apoptosis of melanoma cancer cell lines, treatment of cutaneous leishmaniasis, ulcerous eyelid wounds, corneal infections, sterilization of dental cavities, skin regeneration, etc.

Recent progress in atmospheric plasmas led to creation of cold plasmas with ion temperatures close to room temperature. Cold non-thermal atmospheric plasmas can have tremendous applications in biomedical technology. K. H. Becker, K. H. Shoenbach and J. G. Eden "Microplasma and applications" *J. Phys. D. Appl. Phys.* 39, R55-R70 (2006). In particular, plasma treatment can potentially offer a minimum-invasive surgery that allows specific cell removal without influencing the whole tissue. Conventional laser surgery is based on thermal interaction and leads to accidental cell death i.e. necrosis and may cause permanent tissue damage. In contrast, non-thermal plasma interaction with tissue may allow specific cell removal without necrosis. In particular, these interactions include cell detachment without affecting cell viability, controllable cell death etc. It can be used also for cosmetic methods of regenerating the reticular architecture of the dermis. The aim of plasma interaction with tissue is not to denaturate the tissue but rather to operate under the threshold of thermal damage and to induce chemically specific response or modification. In particular presence of the plasma can promote chemical reaction that would have desired effect. Chemical reaction can be promoted by tuning the pressure, gas composition and energy. Thus the important issues are to find conditions that produce effect on tissue without thermal treatment. Overall plasma treatment offers the advantage that is can never be thought of in most advanced laser surgery. E. Stoffels, I. E Kieft, R. E. J Sladek, L. J. M van den Bedem, E. P van der Laan, M. Steinbuch "Plasma needle for in vivo medical treatment: recent developments and perspectives" *Plasma Sources Sci. Technol.* 15, S169-S180 (2006).

In recent few years cold plasma interaction with tissues becomes very active research topic due to aforementioned potential. Preliminary experiments have demonstrated potent effects of cold plasma treatment on cancerous tissue both in vitro and in vivo and suggest the important role of the reactive oxygen species (ROS) in the selective treatment of cancer. In-vivo efficiency of cold plasmas for ablation of mid-sized subcutaneous bladder cancer tumors on mice was demonstrated. M. Keidar, A. Shashurin, R. Ravi, R. Guerrero-Preston and B. Trink, *British Journal of Cancer* 105, 1295 (2011). Also, selectivity of plasmas for killing of cancerous cells while remaining healthy cells intact was demonstrated in vitro for various cell lines. Cellular level effects include detachment of cells from extracellular matrix and decreasing of migration velocity of cells, while the sub-cellular level effect is the reduction of cell surface integrin expression (receptors responsible for cell adhesion and migration). A. Shashurin, M. Keidar, S. Bronnikov, R. A. Jurjus, M. A. Stepp, *Appl. Phys. Let.* 92, 181501 (2008). A. Shashurin, M. A. Stepp, T. S. Hawley, S. Pal-Ghosh, L. Brieda, S. Bronnikov, R. A. Jurjus, M. Keidar, Influence of cold plasma atmospheric jet on integrin activity of living cells *Plasma Process. Polym.* 7 294 (2010). In addition, it was found that normal and cancer cells respond to CAP differently depending on the where they are in terms of the cell cycle through their various life functions. Migration of normal cells was reduced by 30% (p<0.001), however the cancer cells react differently: more aggressive carcinoma cells showed more response in the decrease of the migration rates (~20% with p<0.001) than less aggressive papilloma cells (p>0.05). It was also found that CAP induces a transient 2-fold G2/M-arrest in papilloma and carcinoma cells; normal epithelial cells did not show any change in cell cycle progression. O. Volotskova, T. S. Hawley, M. A. Stepp & M. Keidar, "Targeting the cancer cell cycle by cold atmospheric plasma," *Scientific Reports,* 2:636, Sep. 6, 2012

Given these findings, cold plasma represents a promising new adjunct for cancer therapy, offering the ability to directly target and selectively kill cancerous cells. CAP can lead to a new paradigm in cancer therapy by offering a minimum-invasive surgery technique that allows specific cell removal without affecting the whole tissue. CAP demonstrated in-vitro and in-vivo highly selective potential towards number of cancer cell line (lung, bladder, head & neck, skin etc.) and, as such, has potential to address limitations of current clinical chemotherapeutic approaches contain with regards to nonselective and incomplete tumor ablation. In addition, CAP action leads to selective decrease in cancer cell migration, thus has potential to mitigate the metastasis and may lead to the development of a novel therapeutic approach for metastasis.

A variety of different electrosurgical generators are known. U.S. Pat. No. 4,429,694 to McGreevy disclosed an electrosurgical generator and argon plasma system and a variety of different electrosurgical effects that can be achieved depending primarily on the characteristics of the electrical energy delivered from the electrosurgical generator. The electrosurgical effects included pure cutting effect, a combined cutting and hemostasis effect, a fulguration effect and a desiccation effect. Fulguration and desiccation sometimes are referred to collectively as coagulation.

Another method of monopolar electrosurgery via argon plasma technology was described by Morrison in U.S. Pat. No. 4,040,426 in 1977 and McGreevy U.S. Pat. No. 4,781, 175. This method, referred to as argon plasma coagulation (APC) or argon beam coagulation is a non-contact monopolar thermoablative method of electrocoagulation that has been widely used in surgery for the last twenty years. In general, APC involves supplying an ionizable gas such as argon past the active electrode to target tissue and conducting electrical energy to the target tissue in ionized pathways as non-arcing diffuse current. Canady described in U.S. Pat. No. 5,207,675 the development of APC via a flexible catheter that allowed the use of APC in endoscopy. These new methods allowed the surgeon, endoscopist to combine standard monopolar electrocautery with a plasma gas for coagulation of tissue.

Yet another system is disclosed in WO 2012/061535 A2, which disclosed a system for simultaneously cutting and coagulating tissue.

SUMMARY OF THE INVENTION

The present invention relates to a system for producing cold atmospheric plasma for killing cancer cells while leaving normal cells unaffected.

In a first preferred embodiment, the present invention is an electrosurgical apparatus having a low frequency (LF) electrosurgical unit. The LF electrosurgical unit has a first connector adapted to connect an input of the low frequency electrosurgical conversion unit to an output of a high frequency electrosurgical generator, a tuned high voltage transformer comprising a ferrite core, a primary coil and a secondary coil, the secondary coil having a larger number of turns than the primary coil, and a second connector adapted to connect an output of the low frequency electrosurgical unit to a cold atmospheric plasma probe. The low frequency electrosurgical unit receives from the high frequency electrosurgical unit electrical energy having a band of frequencies centered around a specific frequency and the tuned high voltage transformer is tuned to a resonant frequency lower than the specified frequency. The apparatus may further comprise a cold plasma probe connected to the second connector of the conversion unit. Further, the second connector for connecting a cold plasma probe may comprise an electro-gas output connector. The apparatus may further comprise an electrosurgical generator, wherein the first connector for connecting the conversion unit to an electrosurgical generator connects to a high-voltage output of the electrosurgical generator and to a patient output of the electrosurgical generator. The low frequency electrosurgical unit further may comprise a gas connector for connecting the low voltage electrosurgical unit to a source of an inert gas. The electrosurgical apparatus may further comprise a gas unit for controlling a flow of inert gas to the low frequency electrosurgical unit. The low frequency module may further comprise a first insulation between the primary coil and the secondary coil and a second insulation between the primary and secondary coils and the ferrite core, wherein the first insulation is greater than the second insulation.

In a second preferred embodiment, the present invention is an electrosurgical apparatus comprising an electrosurgical generator comprising a high frequency (HF) power module and a low frequency (LF) power module. The high frequency power module is adapted to generate an electrical energy having a band of frequencies centered around a first frequency, wherein the electrical energy has a first power as the first frequency and a second power lower than the first power at a second frequency lower than the first frequency. The low frequency power module has an input connected to an output of the high frequency module. The low frequency module comprises a resonant transformer comprising a ferrite core, a primary coil and a secondary coil, the secondary coil having a larger number of turns than the primary coil, wherein the resonant transformer has a resonant frequency equal to the second frequency. The low frequency power module may receive from the high frequency power module electrical energy having a first voltage and a first power and outputs electrical energy having a second voltage and a second power, wherein the second voltage is greater than the first voltage and the second power is less than the first power. The electrosurgical generator further may comprise a high frequency output connector adapted to connect to a high frequency electrosurgical accessory and a low frequency output connector adapted to connect to a cold atmospheric plasma accessory. The electrosurgical apparatus may further comprising a cold atmospheric plasma probe connected to the low frequency output of the electrosurgical generator. The electrosurgical apparatus further may comprise a gas unit for controlling a flow of inert gas to an electrosurgical accessory. The low frequency module further may comprise a first insulation between the primary coil and the secondary coil and a second insulation between the primary and secondary coils and the ferrite core, wherein the first insulation is greater than the second insulation.

In a third preferred embodiment, the present invention is an integrated gas-enhanced electrosurgical generator. The generator comprises a high frequency power module, a low frequency power module and a gas module. The high frequency power module adapted to generate an electrical energy having a band of frequencies centered around a first frequency, wherein the electrical energy has a first power as the first frequency and a second power lower than the first power at a second frequency lower than the first frequency. The low frequency power module having an input connected to an output of the high frequency module. The low frequency module comprises a resonant transformer comprising a ferrite core, a primary coil and a secondary coil, the secondary coil having a larger number of turns than the primary coil, wherein the resonant transformer has a resonant frequency equal to the second frequency. The gas module is adapted to control a flow of an inert gas. The generator further may comprise a first electro-gas connector connected to an output of the high frequency power module and an output of the gas module and a second electro-gas connector connected to an output of the low frequency power module and an output of the gas module. The low frequency power module further may comprise a first insulation between primary coil and the secondary coil and a second insulation between the primary and secondary coils and the core, wherein the first insulation is greater than the second insulation.

In another preferred embodiment, the present invention is a method for generating cold atmospheric plasma. The method comprises the steps of generating high frequency electrical energy having a first frequency and a first power with an electrosurgical generator, converting with a resonant transformer said generated high frequency electrical energy at said first frequency and said first power to low frequency electrical energy having a second frequency lower than said first frequency and a second power lower than said first power, and applying said low frequency electrical energy to an inert gas to produce cold atmospheric plasma. The first frequency, for example, may be greater than or equal to 400 KHz and said second frequency less than or equal to 300 KHz. The first power, for example may be greater than or equal to 70 W and said second Power less than or equal to 10 W. The inert gas may be helium.

Still other aspects, features, and advantages of the present invention are readily apparent from the following detailed description, simply by illustrating a preferable embodiments and implementations. The present invention is also capable of other and different embodiments and its several details can be modified in various obvious respects, all without departing from the spirit and scope of the present invention. Accordingly, the drawings and descriptions are to be regarded as illustrative in nature, and not as restrictive. Additional objects and advantages of the invention will be set forth in part in the description which follows and in part will be obvious from the description, or may be learned by practice of the invention.

BRIEF DESCRIPTION OF THE FIGURES

For a more complete understanding of the present invention and the advantages thereof, reference is now made to the following description and the accompanying drawings, in which.

DETAILED DESCRIPTION OF THE PREFERRED EMBODIMENT

In describing a preferred embodiment of the invention illustrated in the drawings, specific terminology will be resorted to for the sake of clarity. However, the invention is not intended to be limited to the specific terms so selected, and it is to be understood that each specific term includes all technical equivalents that operate in similar manner to accomplish a similar purpose. The preferred embodiment of the invention is described for illustrative purposes, it being understood that the invention may be embodied in other forms not specifically shown in the drawings.

The present invention produces cold plasmas which are thermally harmless for the living biological tissue and cannot cause burns. The cold plasma produced by the present invention, however, is deadly for cancer cells while leaving normal cells unaffected.

Figure 1A:
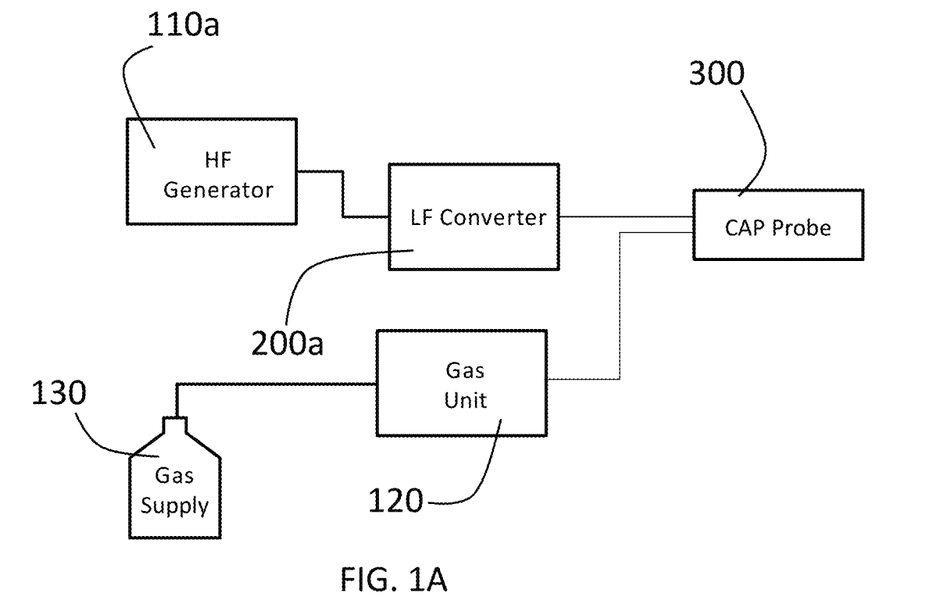
FIG. 1A is a diagram of a first embodiment of a system for producing cold plasmas in accordance with the present invention.

A first embodiment of a system for producing cold plasmas is shown in FIG. 1A. The system has a high frequency (HF) electrosurgical generator or ESU, a low frequency (LF) converter 200, a gas unit 120, a gas supply 130 and a cold atmospheric plasma (CAP) probe 300. The CAP probe 300 is connected to an output of the LF power converter 200 and the gas unit 120. The gas supply 130 is a source of an inert gas such as helium. The gas unit 120 controls the flow of the inert gas to the CAP probe 300. The HF electrosurgical generator 110 supplies high frequency (HF) energy for performing electrosurgical procedures such as electrocautery, argon plasma coagulation and others. The HF energy, for example, may have a frequency of 500 kHz, meaning that the generator outputs energy at a range of frequencies centered at 500 kHz. If the generator is set, for example, at a power of 100 W, the 100 W power at the center frequency of 500 kHz will dominate the signal. Power levels at frequencies surrounding that center frequency will be lower the further those surrounding frequencies are from the center frequency. Conventional electrosurgical generators operate in this manner and would be known to those of skill in the art. In conventional electrosurgical generators, the dominant central frequency typically is in the range of 300 kHz-600 kHz. This dominant central frequency sometimes may be referred to as the "rated frequency."

Figure 2:
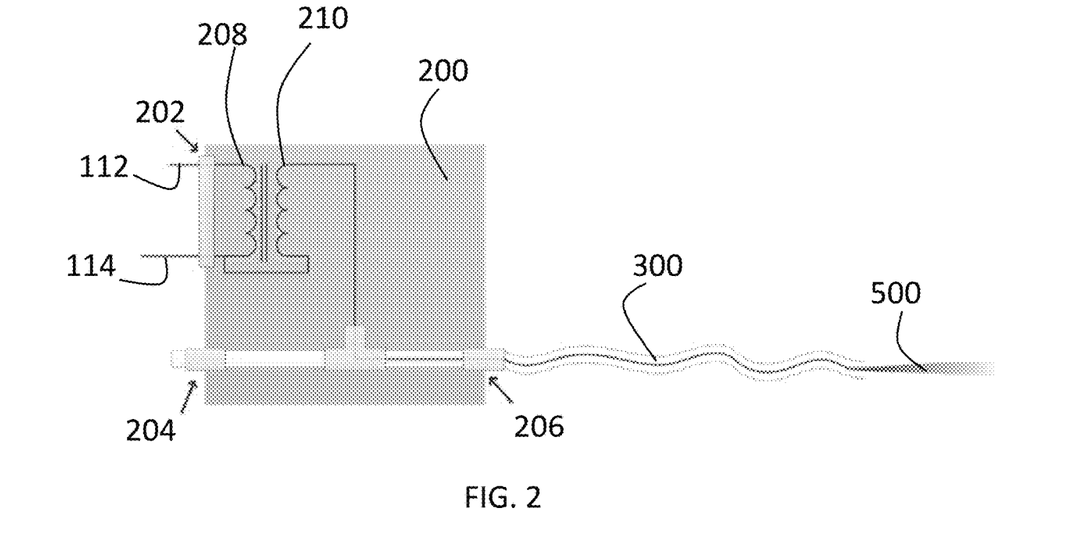
FIG. 2 is a diagram of a low frequency (LF) module and Cold Atmospheric Plasma (CAP) Probe in accordance with a preferred embodiment of the present invention.

The LF converter 200 utilizes a high voltage transformer connected to an output from ESU 110 as shown in FIG. 2. The transformer is a tuned transformer and is tuned to a lower frequency than the central frequency output from the ESU. In other words, the transformer operates as a resonant transformer with a resonant frequency lower than the output frequency of the ESU. For example, if the ESU outputs energy centered at 500 kHz, the transformer may have a resonant frequency of less than 300 kHz.

Figure 3A:
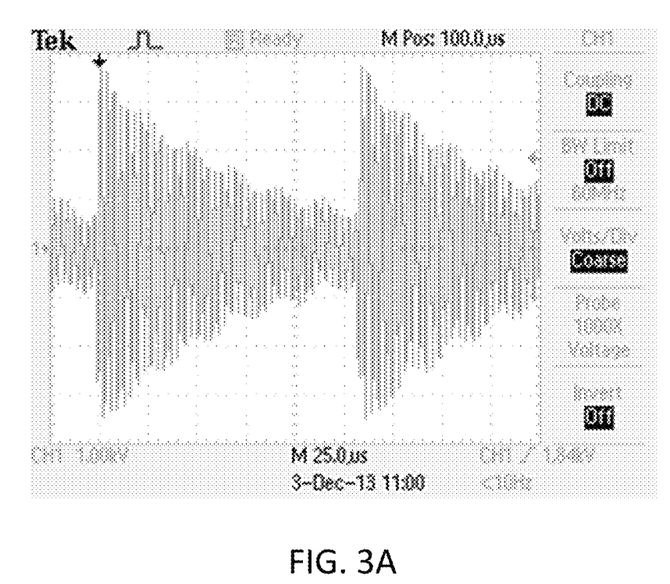
FIGS. 3A and 3B show converted waveforms output from an LF Module in accordance with a preferred embodiment of the present invention.
Figure 3B:
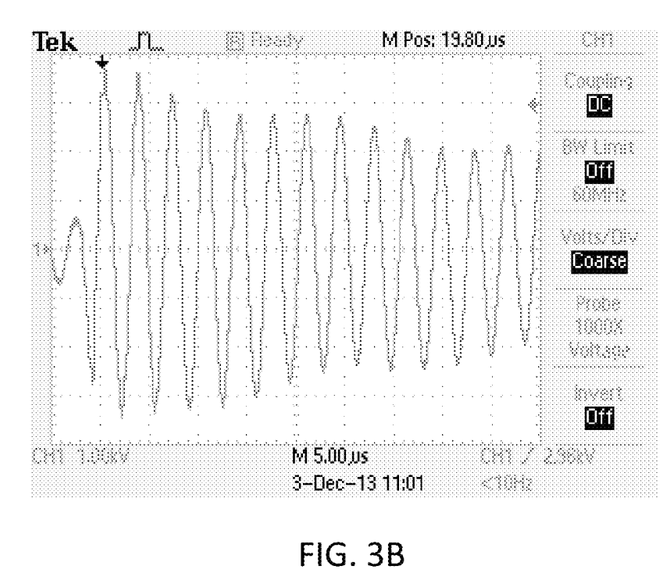
Figure 4:
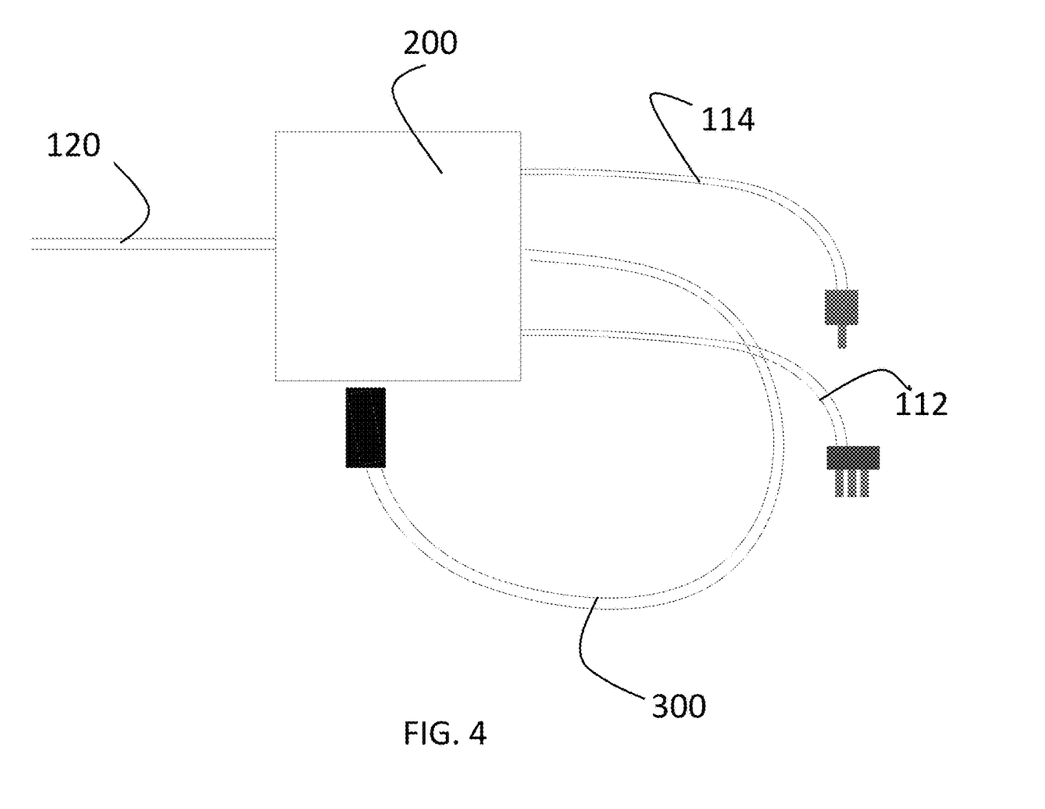
FIG. 4 is an illustration of a LF MODULE with attached CAP Probe in accordance with a preferred embodiment of the present invention.

In a preferred embodiment, the transformer utilizes a primary coil 208 with $N_1=60-70$ turns and secondary coil 210 with about $N_2=300$ turns. The coils are wound on a ferrite core. The specific number of turns utilized in the transformer is given for illustrative purpose only and can be varied in a very wide range. The number $N_2$ should be larger than $N_1$ in order to produce step-up conversion of the voltage. The LF converter output waveform in the preferred embodiment is shown in FIG. 3.

The LF converter up-converts voltage. In the preferred embodiment voltage of about 4 kV is produced. Other embodiments of the LF converter can be used to up-convert the voltage. The output voltage of the LF converter should be in a range 1.5-50 kV.

The LF converter down-converts frequency because the resonant transformer amplifies primarily its own resonant frequency, and, therefore, that resonant frequency dominates the output. In the preferred embodiment an output frequency of about 295 kHz is produced. Outputted frequencies for CAP should be less than about 300 kHz.

The LF converter additionally down-converts power due to the power being lower at the resonant frequency of the transformer and due to load mismatch. In the preferred embodiment, secondary coil can output power <10 Watt even when the ESU is set on a power of 120 W. The LF converter output power should not exceed 20-30 Watt.

A CAP Probe 300 is connected to Electro-Gas output connector 206 of the LF Module. Probe length was about 0.5 meter in the preferred embodiment. However, the present invention is not limited solely to this CAP Probe length, and probe can be up to 5-10 meters long. Output voltage of the transformer should be increased if longer probes are used.

The CAP Probe 300 is made of flexible tube and equipped with wire electrode. The probe 300 may have at its distal end a housing or other structure 310 for use in holding the distal end of the probe. Other structures such as a handle may be used but are not necessary. Wire electrode in the preferred embodiment is located inside the tube. However, it can also be placed outside the tube.

The cold plasma 500 is triggered, for example, by pressing the foot pedal in Coagulation mode. Any Coagulation powers can be used, however increase of the Coagulation Power setting will result in brighter and more intense cold plasma In the preferred embodiment, the CAP Probe has no control buttons on it and cold plasma is turned on directly by pressing the foot pedal. However, the CAP Probe may be equipped with control buttons in order to ignite cold plasma and adjust helium flow by pressing buttons on the CAP Probe itself.

Figure 5A:
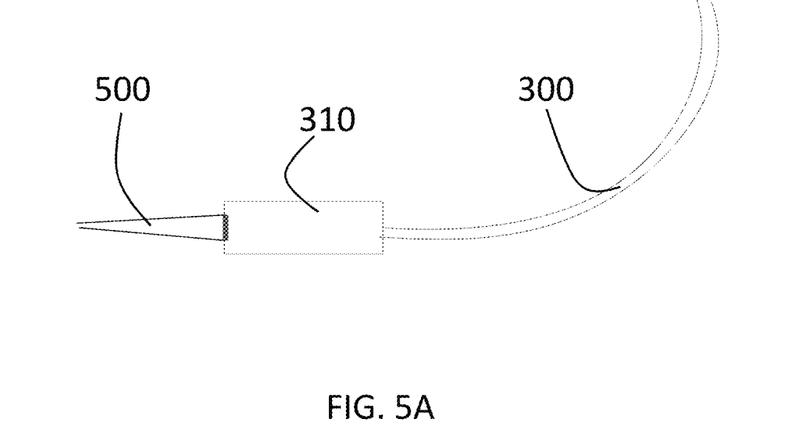
FIG. 5A is an illustration of free cold plasma generated in accordance with a preferred embodiment of the present invention.
Figure 5B:
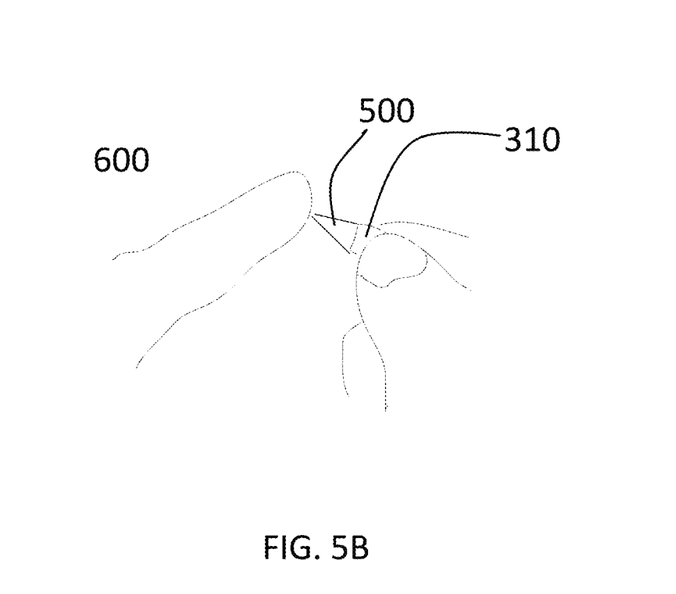
FIG. 5B is an illustration a cold plasma generated in accordance with a preferred embodiment of the present invention in contact with finger.
Figure 6:
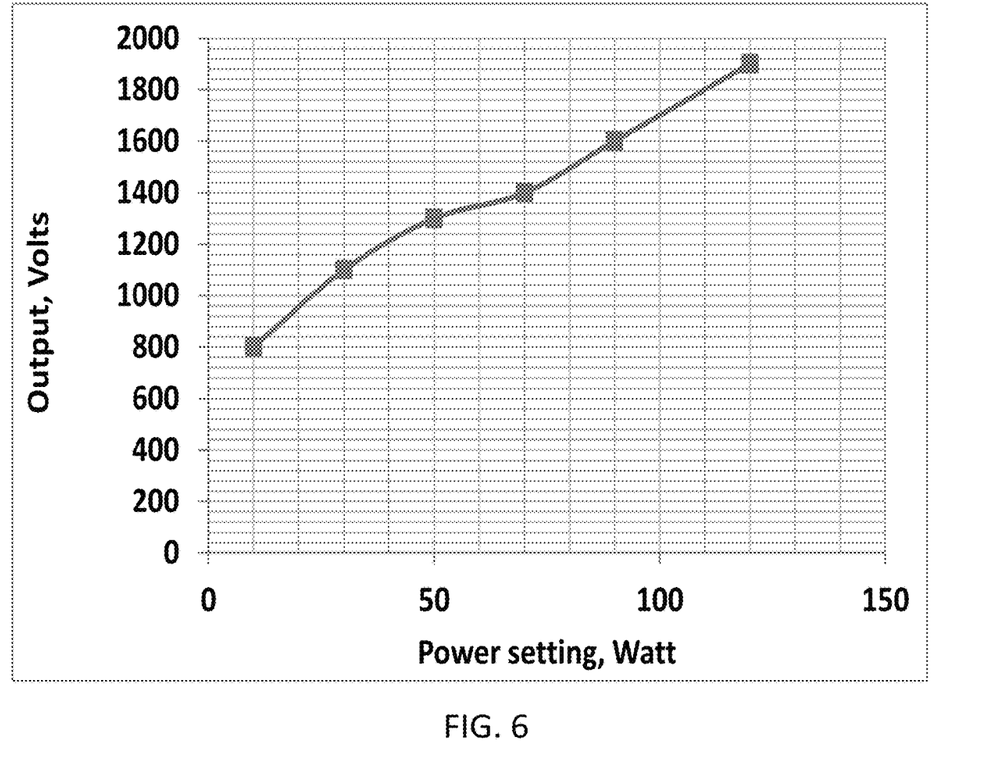
FIG. 6 is a graph of RMS output voltage of Conversion Unit vs. input power setting on an electrosurgical unit (ESU) unit.

The length of free cold plasma jet in experiments was up to 3-4 cm as shown in in FIG. 5A. Placing finger into the cold plasma without any damage is shown in FIG. 5B.

A variety of different configurations of the system are possible. In FIG. 1A the system is set up with the ESU 110, LF converter 200 and gas unit 120 as separate units. With such an arrangement, one could use a conventional electrosurgical generator and conventional gas unit in the system with a converter unit in accordance with the present invention to produce col atmospheric plasma. In FIG. 1A, the CAP probe has a gas connector to connect to the gas unit and an electrical connector to connect to the converter unit.

In another embodiment shown in FIG. 2, the LF converter 200 is equipped with 3 connectors, namely a gas connector 204 (to helium tank 120), an electrical connector 202 (to electrosurgical unit 110) and an electro-gas connector 206 (to CAP probe 300) as shown in FIG. 2.

The gas connector 204 is an input connection. It connects an inert gas such as Helium tank 120 to the LF Module 200 and delivers the inert gas to the LF Module. For example, different grades of the Helium can be used to the helium tank. Flow rates less than 1-15 L/min should be used.

The electrical connector 202 is an input connection. It connects between the ESU 110 and the LF Module 200 and delivers power to the LF Module 200. A high voltage output 112 of the ESU and a patient output 114 of the ESU 110 are used as inputs to the LF Module 200.

The electro-gas connector 206 is the output of the LF Module 200 and is connected to the CAP Probe 300. The electro-gas connector 206 supplies an output electrical signal and helium to the CAP probe.

Figure 1B:
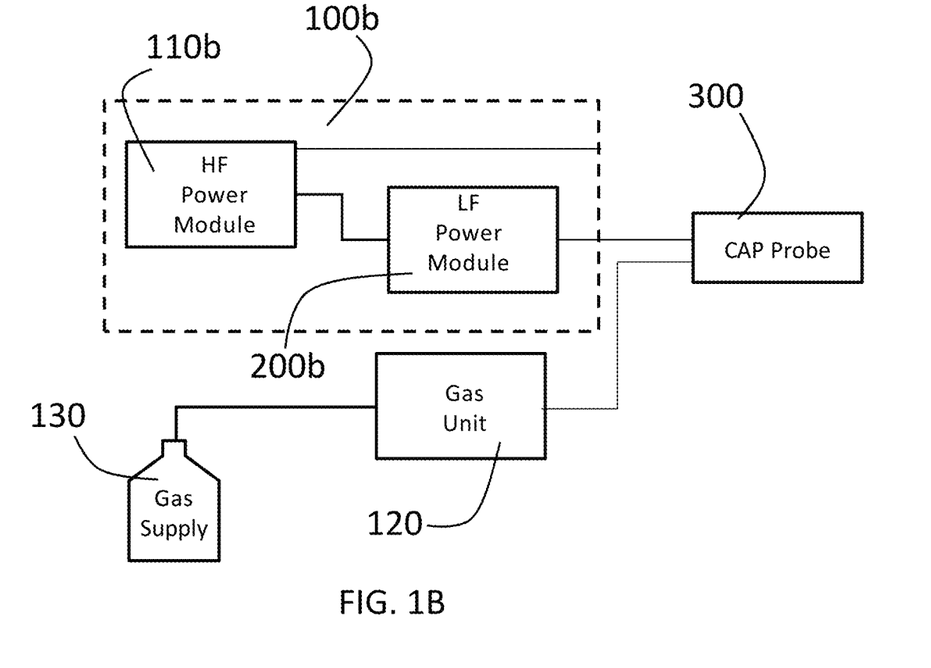
FIG. 1B is a diagram of a second embodiment of a system for producing cold plasmas in accordance with the present invention.

Another embodiment of a system for performing CAP in accordance with the present invention is shown in FIG. 1B. In this embodiment, an electrosurigical generator 100b has an HF module 110b for producing high frequency energy and an LF power module connected to the HF module 110b for converting HF power to LF power for use in CAP. In such an embodiment, the electrosurgical generator may have two electrical output ports, one for CAP and one for HF electrosurgery. The CAP probe would have an electrical connector for connecting to the LF port and the gas connector for connecting to the gas unit.

Figure 1C:
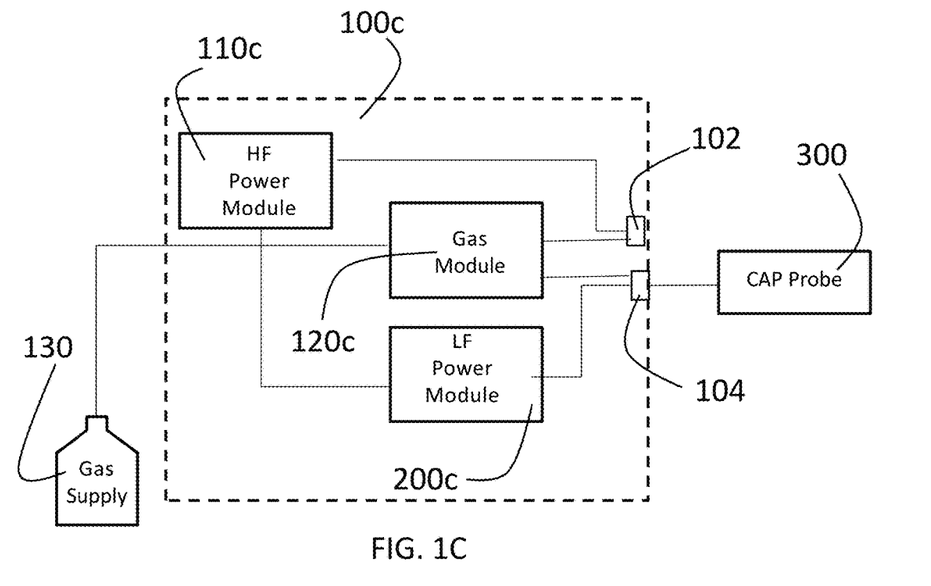
FIG. 1C is a diagram of a third embodiment of a system for producing cold plasmas in accordance with the present invention.

In yet another embodiment shown in FIG. 1C, an integrated gas-enhanced electrosurgical unit 110c has an HF power module 110c, an LF power module 200c, and a gas module 120c. The integrated electrosurgical unit 100c has a plurality of connector ports, for example a port 102 for connecting an argon plasma probe to a gas supply from gas module 120c and power from HF power module 110c and a port 104 for connecting a CAP probe to a gas supply from gas unit 120c and an LF power supply from LF module 200c.

Example

The transformer in the LF Module utilizes primary coil with $N_1$=30 turns of AWG 30 magnet wire and secondary coil with about $N_2$=250 turns of AWG 36 magnet wire. Ferroxcube core UR64/40/20-3C90 was used. Insulation between the windings was up to 10 kV and between the windings to the core—up to 7 kV.

The Conversion Unit in this embodiment produced high voltage with RMS up to about 2 kV and frequency about 150 kHz. Power delivered into cold plasmas was <5 Watt. The dependence of RMS output voltage of Conversion Box vs. input power setting on ESU is show in FIG. 2.

Figure 8:
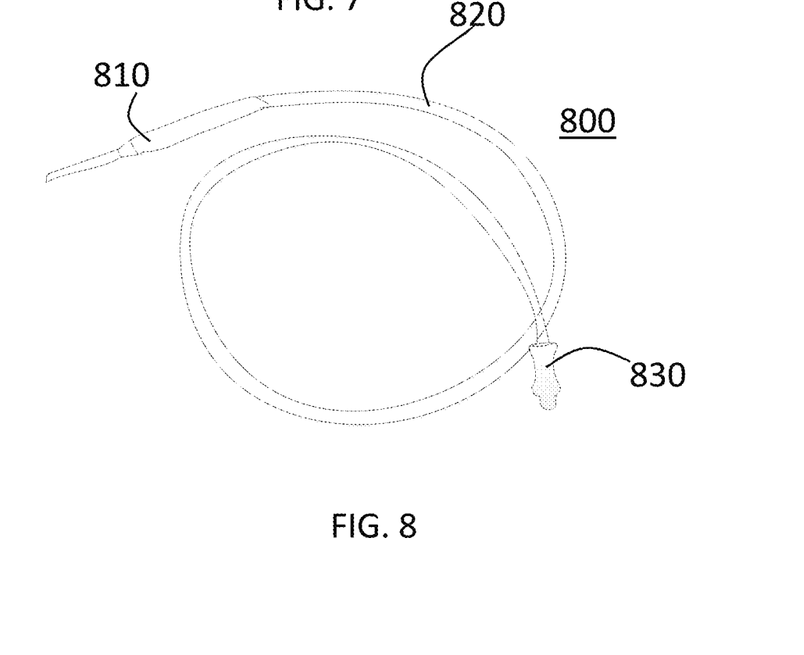
FIG. 8 is a schematic diagram of a CAP Probe in accordance with another preferred embodiment of the present invention.

CAP Probe shown in FIG. 8 can utilize one-electrode or two-electrode configuration. In one-electrode configuration—high voltage electrode can be placed inside the flexible tube used for the Helium supply or embedded in the tube's wall. In two-electrode configuration high voltage electrode is placed inside the tube and grounded shield is embedded in the tube walls.

Figure 7:
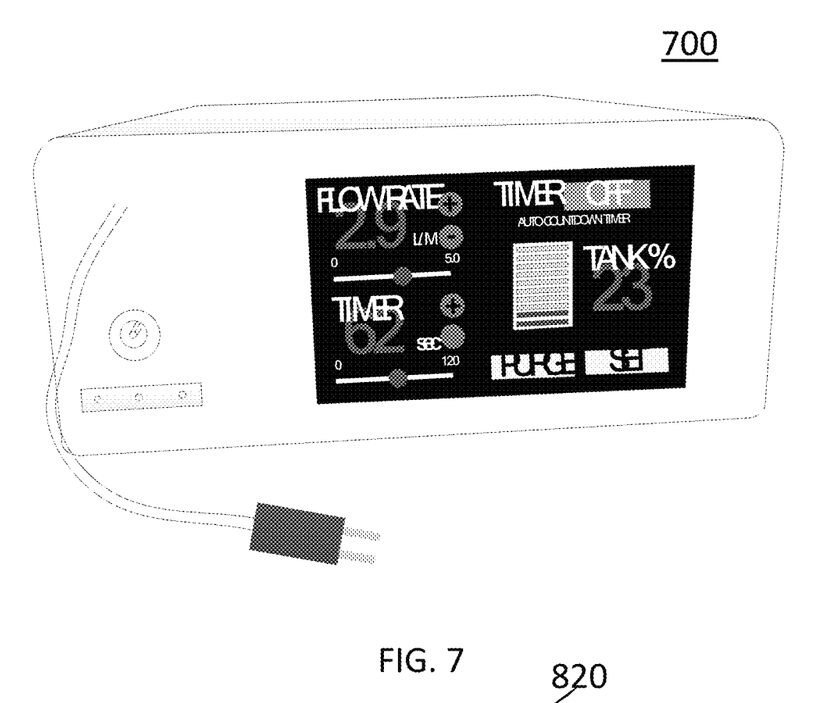
FIG. 7 is a diagram of a Conversion Unit in accordance with another preferred embodiment of the present invention.

The schematic view of the Conversion Box and 3 meter long CAP Probe are shown in FIGS. 7 and 8 respectively. Preferred Helium flow rate for this embodiment was about 5 LPM. The probe 800 has handle 810, an elongated tube 820 and a connector 830 for connecting the probe to the LF Module.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment was chosen and described in order to explain the principles of the invention and its practical application to enable one skilled in the art to utilize the invention in various embodiments as are suited to the particular use contemplated. It is intended that the scope of the invention be defined by the claims appended hereto, and their equivalents. The entirety of each of the aforementioned documents is incorporated by reference herein.

What is claimed is:

1. An integrated gas-enhanced electrosurgical generator comprising:
   a high frequency power module adapted to generate an electrical energy having a band of frequencies centered around a first frequency, wherein said electrical energy has a first power at said first frequency and a second power lower than said first power at a second frequency lower than said first frequency;
   a low frequency power module having an input connected to an output of said high frequency power module, said low frequency module comprising:
      a resonant transformer comprising a ferrite core, a primary coil and a secondary coil, the secondary coil having a larger number of turns than the primary coil, wherein said resonant transformer has a resonant frequency equal to said second frequency; and
   a gas module adapted to control a flow of an inert gas;
   a first electro-gas connector connected to said output of said high frequency power module and an output of said gas module; and
   a second electro-gas connector connected to an output of said low frequency power module and said output of said gas module.

2. An electrosurgical apparatus according to claim 1, wherein said low frequency power module further comprises:
   a first insulation between said primary coil and said secondary coil; and
   a second insulation between said primary and secondary coils and the ferrite core;
   wherein said first insulation is greater than said second insulation.

3. An electrosurgical apparatus according to claim 1, wherein said first frequency is greater than or equal to 400 KHz and said second frequency is less than or equal to 300 KHz.

4. An electrosurgical apparatus according to claim 1, wherein said second frequency is less than 300 kHz.

5. An electrosurgical apparatus according to claim 1, wherein said first power is greater than or equal to 70 W and said second Power is less than or equal to 10 W.

* * * * *